US008375939B2

(12) United States Patent
Sannie et al.

(10) Patent No.: US 8,375,939 B2
(45) Date of Patent: Feb. 19, 2013

(54) SECURED ANESTHETIC DEVICE FOR HIGH RATE MEDICAL SAMPLING ON SMALL LABORATORY ANIMALS

(75) Inventors: Vincent Sannie, Corfelix (FR); Sébastien Sannie, Marolles en Brie (FR)

(73) Assignee: Equipement Veterinaire Minerve, Esternay (FR)

( * ) Notice: Subject to any disclaimer, the term of this patent is extended or adjusted under 35 U.S.C. 154(b) by 990 days.

(21) Appl. No.: 12/444,182

(22) PCT Filed: Jun. 1, 2007

(86) PCT No.: PCT/FR2007/000919
§ 371 (c)(1),
(2), (4) Date: Apr. 3, 2009

(87) PCT Pub. No.: WO2008/040856
PCT Pub. Date: Apr. 10, 2008

(65) Prior Publication Data

US 2010/0006093 A1 Jan. 14, 2010

(30) Foreign Application Priority Data

Oct. 5, 2006 (FR) .................................... 06 08720

(51) Int. Cl.
*A61M 15/00* (2006.01)
(52) U.S. Cl. .................................................. 128/203.12
(58) Field of Classification Search ............. 128/202.12, 128/203.12, 203.15, 202.13, 205.26, 910
See application file for complete search history.

(56) References Cited

U.S. PATENT DOCUMENTS

| | | | | |
|---|---|---|---|---|
| 5,109,797 | A * | 5/1992 | Briant et al. | 119/420 |
| 6,352,076 | B1 * | 3/2002 | French | 128/203.12 |
| 6,354,292 | B1 * | 3/2002 | Fisher | 128/203.12 |
| 6,764,434 | B1 * | 7/2004 | Volk | 483/36 |
| 6,776,158 | B1 | 8/2004 | Anderson et al. | |
| 7,331,341 | B2 * | 2/2008 | Nelson | 128/203.12 |
| 7,367,335 | B2 * | 5/2008 | Fuhrman et al. | 128/203.15 |
| 2003/0209244 | A1 | 11/2003 | Nelson | |
| 2004/0216737 | A1 * | 11/2004 | Anderson et al. | 128/203.12 |
| 2009/0151720 | A1 * | 6/2009 | Inoue et al. | 128/203.12 |
| 2010/0101500 | A1 * | 4/2010 | Sannie et al. | 119/420 |

FOREIGN PATENT DOCUMENTS

| | | |
|---|---|---|
| WO | WO 0074593 A1 * | 12/2000 |
| WO | 03/070308 | 8/2003 |
| WO | 03/079924 | 10/2003 |

* cited by examiner

*Primary Examiner* — Jackie Ho
*Assistant Examiner* — Nyca T Nguyen
(74) *Attorney, Agent, or Firm* — Sutherland Asbill & Brennan LLP

(57) ABSTRACT

The invention relates to a dual wall cylindrical container with a gas distribution source in the lower portion thereof. The cylindrical container is positioned at the lower portion of a frame with two suction sources for potentially pollutant gases. The first source has the highest gas charge and extends from the space defined by the dual wall of the cylinder and is connected to an active-carbon dynamic extraction system. The second source extends from the gap between the upper edge of the open cylinder and the frame, and is connected to a global network for discharging and processing the charged air. A third suction source extends from the two horizontal work planes provided with sieves for suction from the top to the bottom. The gas distribution source is provided with a safety device that cuts off the supply of gases when detecting an abnormality in the suction circuits.

4 Claims, 1 Drawing Sheet

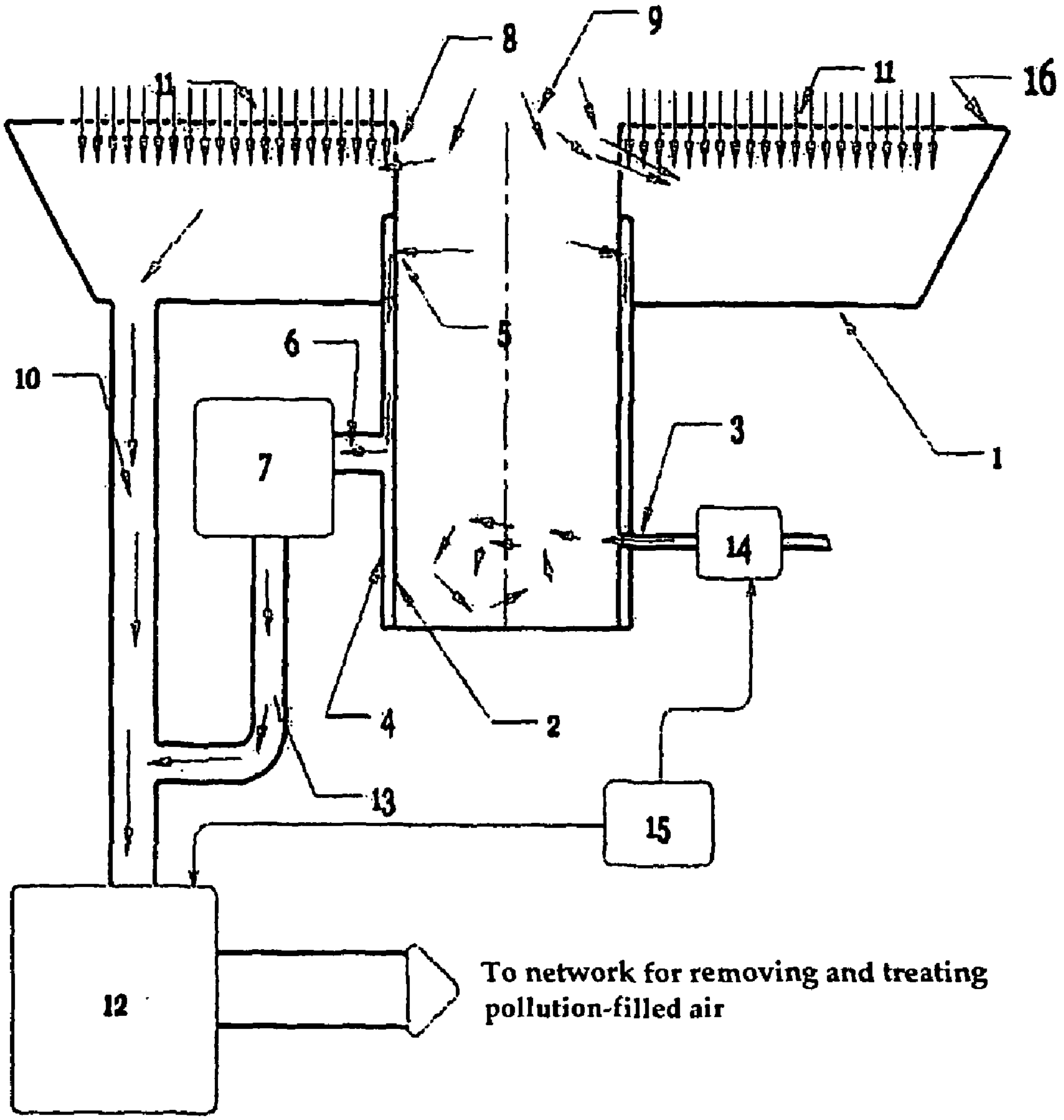
8
9
11
11
16
5
6
10
7
3
1
14
4
2
13
15
12
To network for removing and treating pollution-filled air

SECURED ANESTHETIC DEVICE FOR HIGH RATE MEDICAL SAMPLING ON SMALL LABORATORY ANIMALS

TECHNICAL FIELD OF THE INVENTION

The invention comes within the field of the activities of medical and biological research on small laboratory animals in general, and more particularly within the context of applications associated with pharmacology. These applications require blood samples to be taken from a very large number of rodents anesthetized by inhalation. The operation on the animals needs to be fast and reproducible, while ensuring that the exposure of users to halogen-containing particles is close to zero at best, or within the maximum authorized exposure values at worst. The invention thus incorporates means for collecting residual anesthetic vapor and means for eliminating anesthetic vapor that impregnates the fur of the animals from which samples are taken.

STATE OF THE PRIOR ART

To put a small laboratory animal to sleep, present techniques consisting in using chambers, boxes, or other individual induction devices. Chambers or boxes enable animals to be anesthetized in groups in order to satisfy throughput objectives (taking blood samples from a large number of animals in order to establish statistics concerning results on experimental protocols under study), while also optimizing induction times. Induction chambers or boxes are designed to be filled with an anesthetic gas and then to receive wakeful animals to be anesthetized. Certain kinds of equipment need to be fully emptied before extraction of the animal(s) for treatment. Others do not require complete prior emptying and they enable animal(s) to be extracted manually from a box saturated in halogen-containing compounds and then subsequently to provide an addition of missing gas. The points they have in common include the need to close the receptacle for the operation of filling with halogen-containing gas, followed by an opening operation in order to extract one or more anesthetized animals. That technique presents the major drawback of subjecting the animals for treatment to an anesthetic exposure time that differs depending on whether the sample is taken from the first animal or the last animal extracted from the chamber or box, thereby falsifying experimental conditions and statistical results from one subject to another. Another common practice consists in using certain individual devices for maintaining animals under long duration anesthesia and requiring pre-anesthesia (prior passage of the animal through an induction cage). In order to do this and also satisfy needs for fast execution, the operator ignores the pre-anesthesia stage and constrains the wakeful animal to inhale the anesthetic gas directly from the device (pointing the head of the animal manually towards the source of anesthetic gas coming from the induction tunnel). Although that practice presents the advantage of execution being fast and reproducible, while avoiding impregnating the fur of the animal with anesthetic vapor (since anesthetic is delivered directly to the animal's nose), no account is taken of the stress imposed on the animal or of the risk of the users being bitten.

Certain other individual devices enable anesthetic to be induced directly to the nose of each animal, but they require an additional operator directly performing manipulations associated with anesthetizing animals, while samples are being taken by another operator, so that the overall treatment time is not slowed down. Although experimental conditions are then indeed identical from one subject to another, they do not satisfy economic objectives since two users are needed to perform the manipulations.

Whatever the kinds of equipment used, they are not designed to satisfy needs for reproducibly anesthetizing a large number of animals for treatment in series under satisfactory conditions of speed and cost of execution, while also ensuring safety for the personnel involved.

SUMMARY OF THE INVENTION

The invention is a safe anesthesia device making it possible to manipulate a large number of laboratory animals under short-duration anesthesia. It protects personnel from residual or accidental exposure to halogen-containing vapor, from the beginning of anesthesia to the end of the manipulation operation. It satisfies the working context characterized by precise, fast, and repetitive operations being performed on anesthetized animals. It eliminates the mechanical stresses of manipulations that are not compatible with these characteristics. The invention simultaneously ensures the following functions:

- rapid induction of an anesthetic gas to one or more wakeful rodents placed in a container that does not have an opening or closure system and that is referred to as an "induction cylinder"; and
- collecting and removing (exhausting) residual, accidental, or functional anesthetic coming from accessories, animal fur, or work planes during the manipulations performed after induction, with this being done with the help of a collection and removal device.

Concerning the Induction Cylinder

This is a generally cylindrical container positioned vertically, having a closed bottom and an open top portion through which the animal is inserted and removed. The cylinder presents dimensions adapted to the size and the morphology of the animal such that once inserted therein the animal cannot get out on its own. For reasons of asepsis, it is fitted with an internal lining or other suitable extractable container for single use or capable of being sterilized, making it easier to insert or remove the animal into or from the system. The cylinder is connected to the source of anesthetic gas that delivers anesthetic vapor continuously only, and only if the devices for collecting and removing residual gas are active. Said cylinder, which is continuously saturated in anesthetic gas, enables induction of the animal to be fast, controlled, and reproducible as soon as the animal has been inserted. That same cylinder is contained in a second cylinder of diameter and height that are slightly greater. The space between the inner cylinder and the outer cylinder is connected to an anti-pollution device (a device with active carbon capable of capturing organic solvent). The assembly constituted by the two containers is referred to as an induction cylinder. It is positioned on a horizontal work plane so that the top portion through which the animal is inserted lies in the same plane as the work plane on which the animals are manipulated; which a work plane is itself fitted with devices for collecting and removing residual anesthetic gas.

Concerning the Collection and Removal Device

This device seeks to eliminate any emission of particles of anesthetic gas into the working environment of the operators while animals are being manipulated during post-induction operations.

The device comprises three levels of suction applied to excess anesthetic gas:

- The first level, is filled to the greatest extent with halogen-containing particles, and is performed with a dynamic antipollution device that is itself known, and that is fitted with active carbon filters. The usual technical data recognized as giving the best performance for capturing organic solvents indicates that the travel speed through a column of active carbon situated downstream needs to be close to 0.5 meters per second. Given that requirement, the top portion of the induction cylinder, connected to the antipollution device, thus serves to suck up excess anesthetic agent at a rate that is moderate and that is calculated so as to satisfy this requirement.

The second level of suction, is filled with residual halogen-containing particles coming from the cylinder and not extracted by the first level of suction, and it takes place at the top edge of said cylinder.

The third level of suction, is filled with residual halogen-containing particles coming from the anesthetized animal placed on the work plane for taking samples. The high residual particle suction speed, of the order of 1 meter per second, ensures almost total extraction of the halogen-containing residues impregnating the fur when the animals are extracted from the cylinder. The horizontal work plane is fitted with filter screens enabling a uniform and continuous suction stream to be obtained that flows vertically downwards, thereby avoiding any spread of anesthetic in the working environment of the manipulating personnel.

The second and third levels of residual gas suction are performed using a turbine connected to the network for removing and treating pollution-filled air that is specific to the laboratory. Its suction rate is controlled and varies as a function of the state of clogging of the suction screen. Any anomaly concerning suction rate (excess clogging of the screen) or any anomaly of the system for removing and treating pollution-filled air is taken into account and signaled.

BRIEF SUMMARY OF THE DIAGRAM FIG. 1/1

Presentation of induced gas streams (3) flowing in the cylinder (2), with excess gas being trapped at a first level of suction (5) by an antipollution system (7) using active carbon. The residual gas in the second and third suction levels (8 and 11) is collected in the supporting structure (frame) (1) and then directed towards a network for removing and treating pollution-filled air via the controlled turbine (12) and the suction channel (10). A safety device (15) is fitted to the gas distribution source and it interrupts the arrival (14) of said gas if an anomaly is detected in the polluted gas suction circuits.

DETAILED DESCRIPTION OF AN EMBODIMENT

The entire device is associated with a supporting structure (1) that provides it with stability. The cylinder (2) positioned under the two work planes (16) is closed at its bottom end and open at its top end (9). Near the bottom end of the cylinder (2) there is a channel (3) connected to the source for delivering anesthetic gas, which source is situated upstream from the safety device (15 and 14). The cylinder (2) is placed in the cylinder (4) so that the space (5) that exists between the outside surface of said cylinder (2) and the inside surface of said cylinder (4), and connected to the suction channel (6), is connected to a dynamic antipollution system (7). The antipollution system (7) constituting the first level of residual anesthetic gas suction has a filtered air outlet connected to a pipe (13), itself connected to the suction channel (10). The supporting structure (1) for collecting the other two possible sources of residual polluting gas emanation, has a passage (8) situated at the junction between the two work planes (16) and at the upper periphery of the cylinder (2). It also has two work planes (16) incorporated therein and fitted with suction screens (11). The entire supporting structure (1) is connected to the general network for removing and treating pollution-filled air via the suction turbine (12) connected to the suction channel (10). Said supporting structure (1) thus collects the residual anesthetic gas coming from the suction screens (11) and from the passage (8), thus embodying the other two levels of polluting gas suction. The safety device (15) controls the speed of the turbine (12) and manages operation of the device (14) for closing the halogen-containing gas delivery source in the event of an anomaly of extraction operation being detected.

POSSIBLE INDUSTRIAL APPLICATIONS

The invention can be used in all fields of activity requiring the manipulation of bodies that carry harmful or toxic particles that need to be kept out of the working environment of the manipulators.

We claim:

1. A device enabling anesthetic gas to be induced to a small laboratory animal, wherein said device comprises a supporting structure and a container referred to as an induction cylinder that remains permanently open in its top portion and closed in its bottom portion, said container presenting an inner cylinder and an outer cylinder, a space being defined by the outer periphery of the inner cylinder and by the inner periphery of the outer cylinder, the device also including an introduction channel for continuously introducing a stream of anesthetic agent into said inner cylinder and an extraction system for simultaneously extracting air filled with residual anesthetic gas, said extraction system comprising three calibrated suction levels, namely:

a first suction level in which air filled with residual anesthetic gas coming from the top portion of the inner cylinder is channeled into the space and then directed towards an active carbon antipollution system via an extraction channel;

a second suction level in which air filled with residual anesthetic gas coming from a passage existing between the top edge of the inner cylinder and the supporting structure is channeled into said supporting structure and then directed towards a suction turbine connected to a general network for removing and treating air filled with residual anesthetic gas via a suction channel; and a third level of suction in which air filled with residual anesthetic gas coming from two work planes fitted with calibrated suction screens is channeled into the supporting structure and then directed via the suction channel towards the suction turbine connected to the general network for removing and treating air filled with residual anesthetic gas.

2. A device according to claim 1, wherein the top portion of the container is positioned below the two work planes, which work planes are incorporated in the supporting structure.

3. A device according to claim 1, further including a safety device, said safety device being suitable for detecting an anomaly in the suction of the air filled with residual anesthetic gas, and for interrupting the arrival of anesthetic gas by operating a shutter system for closing the anesthetic agent introduction channel when an anomaly is detected in the suction of air filled with residual anesthetic gas.

4. A device according to claim 1, wherein the active carbon antipollution system is connected to the general network for removing and treating air filled with residual anesthetic gas via suction channels.

* * * * *